(12) United States Patent
Monhart et al.

(10) Patent No.: US 10,888,222 B2
(45) Date of Patent: Jan. 12, 2021

(54) SYSTEM AND METHOD FOR VISUAL FIELD TESTING

(71) Applicants: Carl Zeiss Meditec, Inc., Dublin, CA (US); CARL ZEISS MEDITEC AG, Jena (DE)

(72) Inventors: Matthias Monhart, Winterthur (CH); Maximilian Stocker, Donzdorf (DE); Robert J. Wood, Naples, FL (US)

(73) Assignees: CARL ZEISS MEDITEC, INC., Dublin, CA (US); CARL ZEISS MEDITEC AG, Jena (DE)

( * ) Notice: Subject to any disclaimer, the term of this patent is extended or adjusted under 35 U.S.C. 154(b) by 162 days.

(21) Appl. No.: 16/094,850

(22) PCT Filed: Apr. 20, 2017

(86) PCT No.: PCT/EP2017/059450
§ 371 (c)(1),
(2) Date: Oct. 18, 2018

(87) PCT Pub. No.: WO2017/182596
PCT Pub. Date: Oct. 26, 2017

(65) Prior Publication Data
US 2019/0142270 A1 May 16, 2019

Related U.S. Application Data

(60) Provisional application No. 62/326,332, filed on Apr. 22, 2016.

(51) Int. Cl.
*A61B 3/113* (2006.01)
*A61B 3/024* (2006.01)
(Continued)

(52) U.S. Cl.
CPC ............ *A61B 3/113* (2013.01); *A61B 3/0008* (2013.01); *A61B 3/0041* (2013.01);
(Continued)

(58) Field of Classification Search
CPC .......... A61B 3/113; A61B 3/024; A61B 3/08; A61B 3/0091; A61B 3/11; A61B 3/032;
(Continued)

(56) References Cited

U.S. PATENT DOCUMENTS 5,026,151 A 6/1991 Waltuck et al.
5,094,524 A 3/1992 Fuhr
(Continued)

FOREIGN PATENT DOCUMENTS

DE 4326760 A1 3/1995
DE 19502337 A1 8/1996
(Continued)

OTHER PUBLICATIONS

Chan, Adrian Dart Cheong, "Head-Mounted Perimetry", Master Thesis Submission, Institute of Biomaterials and Biomedical Engineering University of Toronto, 1999, 135 pages.
(Continued)

*Primary Examiner* — Tuyen Tra
(74) *Attorney, Agent, or Firm* — Morrison & Foerster LLP

(57) ABSTRACT

A system and a method for testing a visual field of a subject are described. The method includes determining inter-eye distance of the subject. Visual stimuli are displayed on a left display region and a right display region of a two-dimensional display to the subject based on the determined inter-eye distance. The left display region is configured to display content specific to the left eye and the right display region is configured to display content specific to the right eye of the subject. Subject responses to the visual stimuli are
(Continued)

tracked. Based on the subject responses, a condition of the visual field of each eye the subject is evaluated and then results of the evaluation describing the subject's visual field condition is reported or stored.

21 Claims, 11 Drawing Sheets

(51) Int. Cl.
*A61B 3/08* (2006.01)
*A61B 3/00* (2006.01)
*A61B 3/11* (2006.01)
*A61B 3/032* (2006.01)
*A61B 3/10* (2006.01)
*G02B 27/00* (2006.01)
*G02B 27/01* (2006.01)
*G06F 3/01* (2006.01)
*G06T 19/00* (2011.01)

(52) U.S. Cl.
CPC ............ *A61B 3/0091* (2013.01); *A61B 3/024* (2013.01); *A61B 3/032* (2013.01); *A61B 3/08* (2013.01); *A61B 3/1005* (2013.01); *A61B 3/11* (2013.01); *G02B 27/0093* (2013.01); *G02B 27/0172* (2013.01); *G06F 3/012* (2013.01); *G06F 3/017* (2013.01); *G06T 19/006* (2013.01)

(58) Field of Classification Search
CPC ... A61B 3/0008; A61B 3/0041; A61B 3/1005; G02B 27/0093; G02B 27/0172; G06F 3/012; G06F 3/017; G06T 19/006
USPC ........................................ 351/200, 205, 209
See application file for complete search history.

(56) References Cited

U.S. PATENT DOCUMENTS

| | | |
|---|---|---|
| 5,151,722 A | 9/1992 | Massof et al. |
| 5,550,602 A | 8/1996 | Braeuning |
| 5,565,949 A | 10/1996 | Kasha, Jr. |
| 5,737,060 A | 4/1998 | Kasha, Jr. |
| 5,864,384 A | 1/1999 | McClure et al. |
| 5,880,812 A | 3/1999 | Solomon |
| 5,898,474 A | 4/1999 | McClure et al. |
| 5,910,834 A | 6/1999 | McClure et al. |
| 5,912,723 A | 6/1999 | Maddess |
| 5,920,374 A | 7/1999 | Vaphiades et al. |
| 5,956,124 A | 9/1999 | Dan |
| 6,027,217 A | 2/2000 | McClure et al. |
| 6,033,076 A | 3/2000 | Braeuning et al. |
| 6,045,227 A | 4/2000 | Stewart et al. |
| 6,145,991 A | 11/2000 | McClure et al. |
| 6,149,272 A | 11/2000 | Bergner et al. |
| 6,290,357 B1 | 9/2001 | Massengill et al. |
| 6,386,706 B1 | 5/2002 | McClure et al. |
| 6,494,578 B1 | 12/2002 | Plummer et al. |
| D472,637 S | 4/2003 | Cooper et al. |
| 6,592,222 B2 | 7/2003 | Massengill et al. |
| 7,367,671 B2 | 5/2008 | Sabel |
| 7,446,941 B2 | 11/2008 | Fukuda |
| 7,448,751 B2 | 11/2008 | Kiderman et al. |
| 7,486,341 B2 | 2/2009 | Hong et al. |
| 7,682,021 B2 | 3/2010 | Sabel |
| 7,740,592 B2 | 6/2010 | Graham et al. |
| 7,753,524 B2 | 7/2010 | Sabel |
| 7,972,278 B2 | 7/2011 | Graham et al. |
| 8,075,134 B2 | 12/2011 | Tanassi et al. |
| 8,333,475 B2 | 12/2012 | Sugio et al. |
| 8,371,696 B2 | 2/2013 | Johansson |
| 8,550,626 B2 * | 10/2013 | Griggio ................ A61B 3/0091 351/206 |
| 8,568,311 B2 | 10/2013 | LaPlaca et al. |
| 8,668,334 B2 | 3/2014 | Krenik |
| 8,696,126 B2 | 4/2014 | Yoo et al. |
| 8,931,905 B2 | 1/2015 | Lewis |
| 8,950,864 B1 | 2/2015 | Massengill |
| 2003/0158497 A1 | 8/2003 | Graham et al. |
| 2007/0200927 A1 | 8/2007 | Krenik |
| 2009/0153796 A1 | 6/2009 | Rabner |
| 2010/0118264 A1 | 5/2010 | Sabel |
| 2010/0292999 A1 | 11/2010 | Verma |
| 2011/0205167 A1 | 8/2011 | Massengill |
| 2011/0267577 A1 | 11/2011 | Verma |
| 2013/0194389 A1 | 8/2013 | Vaught et al. |
| 2013/0285885 A1 | 10/2013 | Nowatzyk et al. |
| 2013/0308099 A1 | 11/2013 | Stack |
| 2014/0085282 A1 | 3/2014 | Luebke et al. |
| 2014/0192326 A1 | 7/2014 | Kiderman et al. |
| 2016/0007849 A1 | 1/2016 | Krueger |
| 2017/0290505 A1 | 10/2017 | Correns et al. |

FOREIGN PATENT DOCUMENTS

| | | |
|---|---|---|
| DE | 19540802 A1 | 5/1997 |
| JP | 4103829 B2 | 6/2008 |
| JP | 4169881 B2 | 10/2008 |
| JP | 2009-268778 A | 11/2009 |
| JP | 2011-224213 A | 11/2011 |
| JP | 5141522 B2 | 2/2013 |
| JP | 2016-154149 A | 8/2016 |
| WO | 2006/012679 A1 | 2/2006 |
| WO | 2010/117386 A1 | 10/2010 |
| WO | 2015/120438 A1 | 8/2015 |
| WO | 2016/046202 A1 | 3/2016 |

OTHER PUBLICATIONS

Fidopiastis et al., "Quantitative Assessment of Visual Acuity in Projective Head Mounted Displays", Proceedings of SPIE, vol. 5079, 2003, pp. 399-406.
Hollander et al., "Use of a Portable Head Mounted Perimetry System to Assess Bedside Visual Fields", The British Journal of Ophthalmology, vol. 84, 2000, pp. 1185-1190.
International Preliminary Report on Patentability received for PCT Patent Application No. PCT/EP2017/050959, dated Aug. 2, 2018, 8 pages.
International Preliminary Report on Patentability received for PCT Patent Application No. PCT/EP2017/059450, dated Nov. 1, 2018, 7 pages.
International Search Report and Written Opinion Received for PCT Application No. PCT/EP2017/050959, dated Apr. 6, 2017, 10 pages.
International Search Report and Written Opinion received for PCT Patent Application No. PCT/EP2017/059450, dated Jul. 21, 2017, 10 pages.
Lanman et al., "Near-Eye Light Field Displays", ACM Transactions on Graphics, vol. 32, No. 6, Nov. 2013, 10 pages.
Tel Aviv University, "Virtual Reality Goggles Create an Equal Opportunity Eye Test", ScienceDaily, Available Online at <www.sciencedaily.com/releases/2008/08/080808104929.htm>, Aug. 13, 2008, pp. 1-3.
Wroblewski et al., "Development and Testing of a Novel Head-Mounted, Eye-Tracking Perimeter with Virtual Reality Visor", Doheny Eye Institute and BioFormatix Inc., Presented at American Glaucoma Society Meeting, 2011, 1 page.

* cited by examiner (Prior-art)

(Prior-art)

_US 10,888,222 B2_

SYSTEM AND METHOD FOR VISUAL FIELD TESTING

PRIORITY

This application is a National Phase application under 35 U.S.C. § 371 of International Application No. PCT/EP2017/059450, filed Apr. 20, 2017, which claims priority to U.S. Provisional Application Ser. No. 62/326,332, filed Apr. 22, 2016, the contents of which are hereby incorporated by reference.

BACKGROUND

Testing visual fields i.e., assessing the sensitivity for contrast and other functions of the visual system, is a standard in eye care especially in glaucoma diagnosis and follow up. Visual field testing is typically performed by displaying stimuli to a subject and detecting their response using large instruments one eye at a time (since defects in one eye could be compensated by the other eye). For instance, FIG. 1 shows a traditional bowl-based visual field testing system. A subject 101 is shown observing a hemispherical projection screen 102. The subject is instructed to fixate at a point at the center 103 of the hemispherical screen 102. A projector 104 under control of a processor 105 projects a series of test stimuli of varying sizes and intensities 106 onto different locations on the screen. The subject 101 indicates that a stimulus 106 was seen by depressing button 107. The response is recorded by processor 105 which further functions to evaluate the visual field of an eye based on the subject responses. A camera 108 is used to capture the gaze of the patient throughout the test. The images from the gaze camera 108 are displayed on display 110 to a clinician for aid in patient alignment or test verification.

One other type of visual field testing system is a screen-based testing system (see for example U.S. Pat. Nos. 8,371,696; 5,912,723; and D472637, each of which are hereby incorporated by reference). U.S. Pat. No. 8,931,905 (hereby incorporated by reference) describes a method of testing visual field of a subject on a two-dimensional display screen as shown in FIG. 2. As depicted, a two-dimensional display screen 2 displays a two-dimensional image 4 at a fixed distance from the eyes 8 and 10 of a viewer. While watching the two-dimensional image 4, the viewer's eyes can be monitored to determine various ocular properties and visual field conditions of the viewer.

Some of the drawbacks and/or limitations that are associated with the above discussed or existing visual field systems are that: bowl-based systems are typically large in size and lack portability because of which testing has to be performed on-site and under the supervision of an instrument operator; an eye camera or a gaze tracker is often used for verifying whether a subject is looking at a fixation target during examination or not; a response button (e.g., mechanical clicker) is typically used as a primary means of a subject's feedback to a visual stimulus. Other means of subject response, particularly motion related responses are not currently incorporated into such systems; a system has to be physically moved or mechanically adjusted for displaying content specific to the left or the right eye. This is because of varying inter-eye distance (i.e., horizontal and/or vertical distance between the two eyes) among individuals, which is currently not taken into account during the course of the visual field testing. Horizontal inter-eye distance in adults typically varies in a range of 55 to 75 mm, and typically, the non-examined eye (i.e., eye not undergoing test or not being examined) is covered with an eye patch during examination (see for example, U.S. Pat. No. 5,094,524). This eye patch does not allow the non-examined eye to receive the same amount of ambient light as the other eye and therefore it goes through dark and light adaptation cycles, which also influences the examined eye during the testing cycles, resulting in degraded test accuracy.

Here we describe an improved visual testing system and a method for testing a visual field condition of a subject that overcomes the limitations discussed above.

SUMMARY

According to one aspect of the subject matter described in the present application, a method of performing a visual field test of a subject includes determining inter-eye distance of the subject; displaying visual stimuli on a left display region and a right display region of a two-dimensional display based on the determined inter-eye distance, said left display region configured to display content specific to the left eye and said right display region configured to display content specific to the right eye of the subject; tracking subject responses to the visual stimuli; evaluating the visual field of each eye of the subject based on the subject responses; and reporting or storing results of the evaluation describing the subject's visual field condition or a further analysis thereof.

Further aspects include various additional features and operations associated with the above and following aspects and may further include, but are not limited to corresponding systems, methods, apparatus, and computer program products.

The invention discussed herein is advantageous in a number of respects. For instance, the invention 1) takes into account different inter-eye distance (horizontal and/or vertical) among individuals for visual field testing without the need for mechanical adjustment, 2) allows 100% control of fixation without a camera, 3) eliminates the need for an eye patch, 4) allows use of inexpensive displays for visual testing by enhancing the usable perceived luminance scale resolution, 5) tracks physical motion (e.g. a slight nod or head movement) as a subject response to a visual stimulus, and 6) presents the test results in a new and intuitive way to the examined person.

The features and advantages described herein are not all-inclusive and many additional features and advantages will be apparent to one of ordinary skill in the art in view of the figures and description. Moreover, it should be noted that the language used in the specification has been principally selected for readability and instructional purposes and not to limit the scope of the inventive subject matter.

BRIEF DESCRIPTION OF THE DRAWINGS

FIG. 7A shows what parts of the image (FIG. 7B) will be perceived or not perceived by each eye of a subject having a certain visual field condition.

DETAILED DESCRIPTION

System Overview

Figure 3:
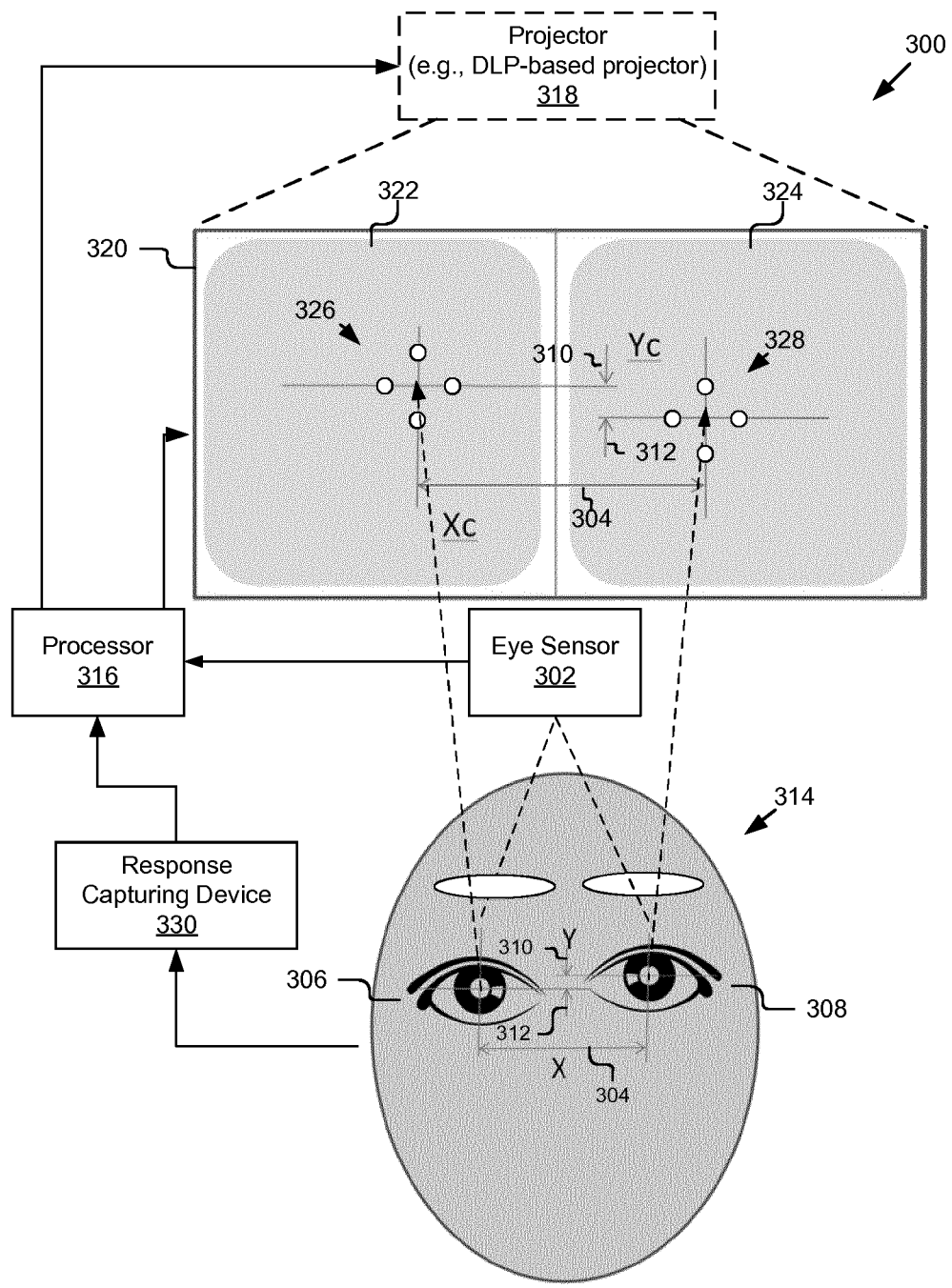
FIG. 3 is an example system for testing visual field of a subject according to one aspect of the present invention.
Figure 12A:
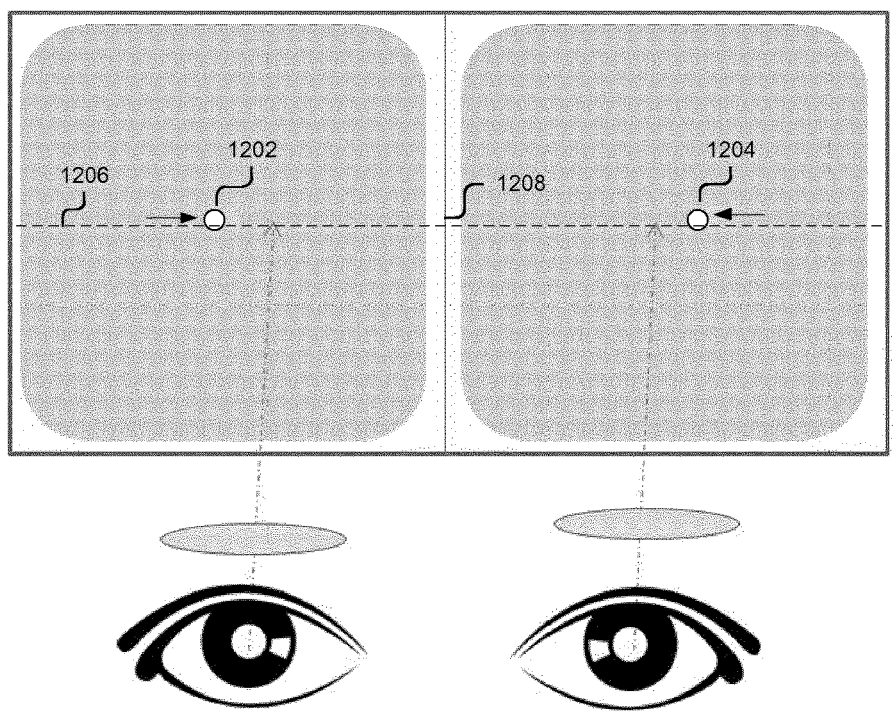
FIG. 12A is an example illustration of subjective measurement of inter-eye distance of a subject based on two moving light dots along a horizontal axis.
Figure 12B:
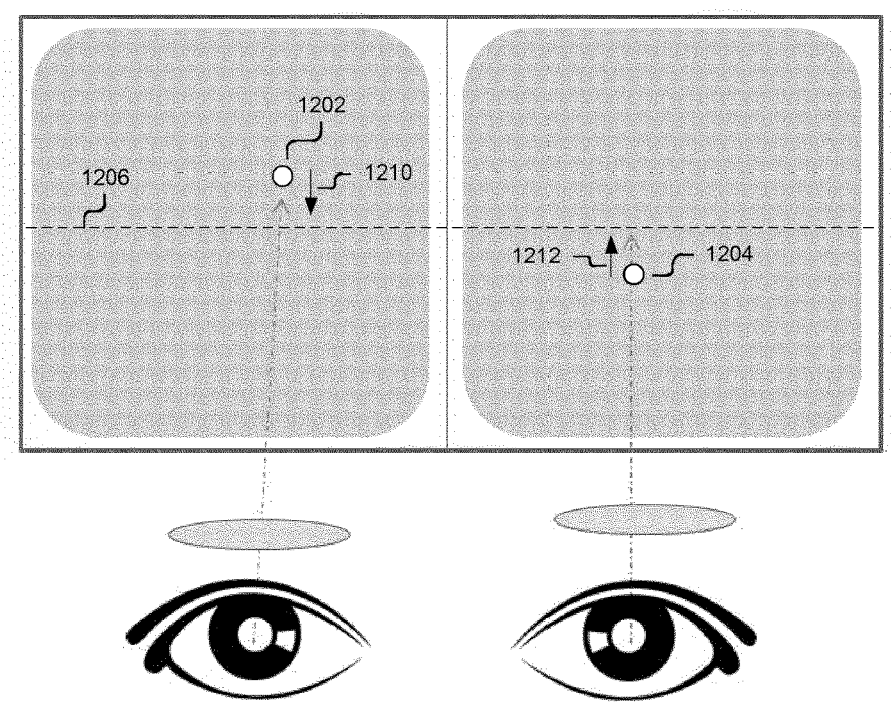
FIG. 12B depicts a scenario where the subject was not able to perceive the two dots on the same horizontal axis.

FIG. 3 illustrates an example system 300 for testing visual field of a subject according to one aspect of the present invention. As depicted, the system 300 includes an eye sensor 302 for measuring horizontal inter-eye distance 304 between a left eye 306 and a right eye 308 (subject is facing into the plane of the paper), and/or vertical inter-eye distance (distance between positions 310 and 312) of the eyes of a subject 314. In one embodiment, this measurement can be accomplished by moving two light dots, one for each eye, (i.e., left dot for left eye and right dot for right eye) towards each other along a horizontal axis, as shown for example by the moving dots 1202 and 1204 along the horizontal axis 1206 in FIG. 12A. These light dots are shown to the subject on a display screen 320 and can be projected directly or via a projector 318. It should be noted that instead of using dots, more complex targets or images may be used to establish the inter-eye distance. The subject gives a response using a response capturing device 330 (e.g., a mechanical clicker, a mouse click, etc.) when the two dots 1202 and 1204 appear on top of each other to the subject (on a hypothetic vertical line, such as the vertical line 1206). In some instances, if the subject, due to squint, was not able to perceive the two dots on the same horizontal axis 1206 then the two dots 1202 and 1204 can be moved from the top down for one eye (see for example, arrow 1210 in FIG. 12B) and from the bottom up for the other eye (see for example, arrow 1212 in FIG. 12B) to measure the vertical inter-eye distance. Again, the subject may push a response button or may use any other kind of signaling when the two dots 1202 and 1204 appear to the subject as converging into one.

Figure 13:
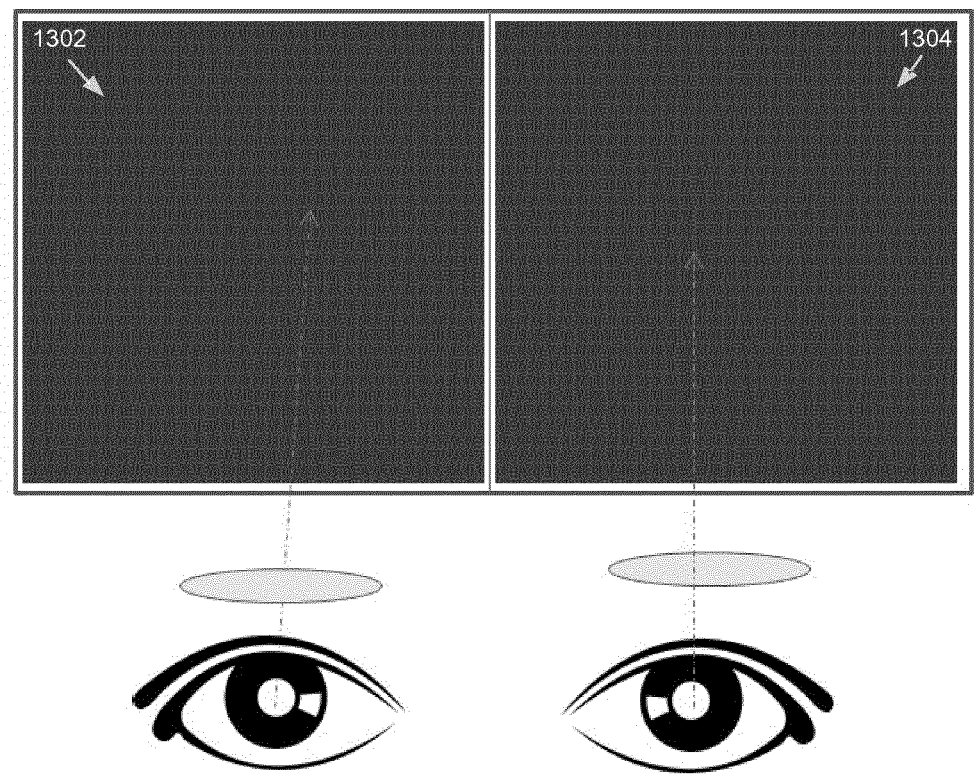
FIG. 13 is an example illustration of an objective measurement of inter-eye distance of a subject.

In another embodiment, one or more components of the system 300 may automatically determine the inter-pupillary distance (IPD) (also referred to generally as the inter-eye distance) without involving subject's response by displaying a fine grid (the lines must be well distinguishable) to each eye of the subject as shown in FIG. 13. In this case, the subject's eyes will converge the two grids 1302 and 1304 on top of each other by finding a mutual fixation based on their personal best accommodation (focus) and convergence. The eye sensor 302 tracks the subject's eyes and gaze direction. For instance, the gaze direction may be calculated based on the pupil position and the positions of the corneal reflexes of infrared LEDs used for the illumination of the eye with invisible light. Based on the gaze direction, one can calculate the IPD and therefore the individual offset for the fixation position as needed in subsequent testing. In some instances, the offset may be fixed or in other words the offset may be calculated based on a fixed convergence (i.e., display being located at a certain fixed virtual distance).

It should be noted that while the subject 314 appears to be front facing in FIG. 3 and/or in the FIGS. 5, 6, 7A, and 7B, in reality, the eyes 306 and 308 are facing towards the display screen (into the plane of the paper) during the course of a visual field test. The eyes are shown in the figures for the purpose of illustrating the concept of inter-eye distance and/or eye positions. Furthermore, reference numeral 306 indicating the subject's left eye and reference numeral indicating 308 indicating the subject's right eye are invertedly referred here for the explanation purposes. The eye sensor 302 is capable of observing and/or recording both eyes of the subject 304 simultaneously. In some embodiments, the eye sensor 302 is further capable of providing information about the pupil diameter and/or position, which can be used to adjust the brightness or luminance level of a display background (e.g., display background 502 or 504 in FIG. 5) or content (e.g., visual stimuli 326 or 328 in FIG. 3). Adjusted brightness may reduce the effect of the pupil size on variability in the results or to compensate the viewing angle of the subject.

The horizontal and/or vertical inter-eye distance measurements are processed by a processor 316 to generate visual stimuli and fixation targets on a display screen, such as the display screen 320. The display screen 320, as depicted, includes a left display region 322 for showing content 326 (e.g., fixation target and/or visual stimuli) specific to left eye 306 of the subject 314 and a right display region 324 for showing content 328 specific to the right eye 308 of the subject 314. A fixation target and visual stimuli with respect to the fixation target for each eye are shown in the corresponding display region according to the inter-eye distance 304 and/or vertical positions 310 and 312 of the subject eyes. If a subject's inter-eye distance (horizontal and/or vertical) is not taken into account and/or the deviation from a standard average setting is too large, then the subject may need to concentrate stronger to match the images displayed in the left and right display regions in his/her brain which potentially may lead to headaches and/or nausea.

In the case depicted in FIG. 3, the subject's eyes are not aligned along the same horizontal axis and are vertically displaced relative to one another as indicated by vertical eye positions Y 310 and 312. In such cases, the visual stimuli are presented to the subject considering these differing vertical eye positions. For instance, the visual stimuli 326 is positioned according to the eye position Y 310 for the left eye 308 (when the eye is facing towards the display screen (i.e., into the plane of the paper)) and the visual stimuli 328 is positioned according to the eye position Y 312 for the right eye 306 (when the eye is facing towards the display screen). The two visual stimuli 326 and 328 are horizontally spaced apart based on the inter-eye distance X 304.

Figure 8:
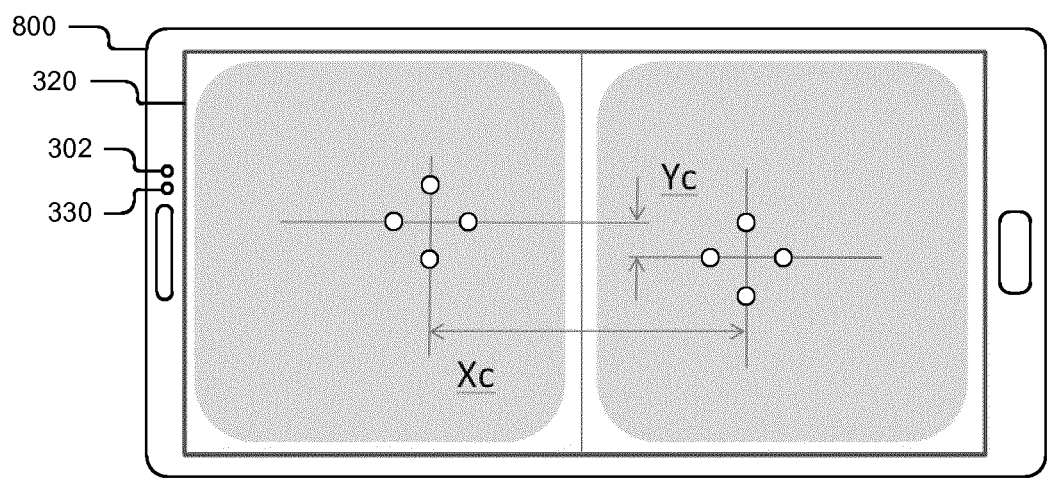
FIG. 8 depicts an example display device that can be used for visual field testing of a subject.

The processor 316 can project the generated fixation targets and/or visual stimuli on the display screen 320 via an optional projector 318 (e.g., a DLP projector) or can present them directly on the display screen 320. For instance, a smartphone includes the processor 316 and the display screen 320 (see for example, the smartphone 800 in FIG. 8)

and the processor 316 may present content processed by it on the display screen 320 of the smartphone directly. In some embodiments, the display screen 320 can be any of a conventional display type, such as organic light-emitting diode (OLED) display, a liquid crystal display (LCD), IPS, TFT, AMOLED, etc. Non-limiting examples of the display screen can be a smartphone screen (see FIG. 8), a computer monitor screen, a television screen, a laptop display screen, a tablet screen, etc. Other types and and/or forms of display screens that are standard and known to one skilled in the art are also possible and are within the scope of this disclosure.

Although a single display screen 320 is shown comprising the two separate regions (i.e., the left display region 322 and the right display region 324), it should be noted that two separate display screens can be used to show content (e.g., visual stimuli) specific to each eye of the subject 314. In some embodiments, the display screen 320 can be comprised within a virtual reality headset that enables the subject 314 to experience content in a virtual reality environment, as discussed in further detail below with respect to FIG. 9.

Figure 1:
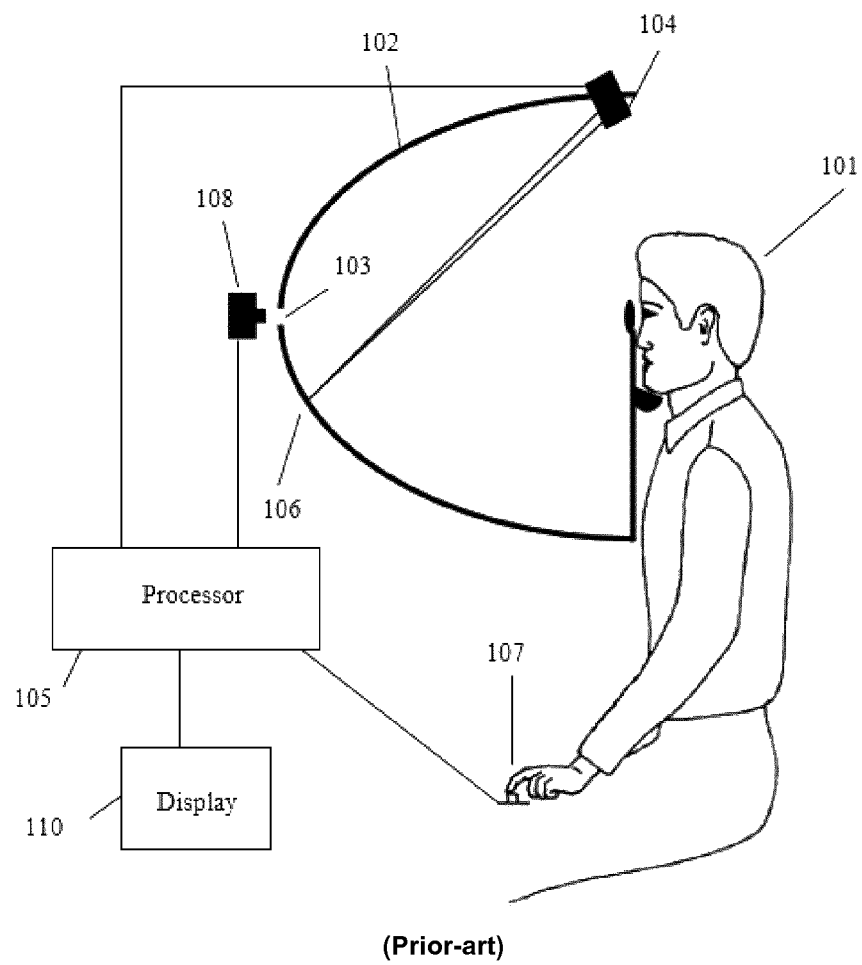
FIG. 1 is an example illustration of a prior-art bowl-based visual field system.
Figure 2:
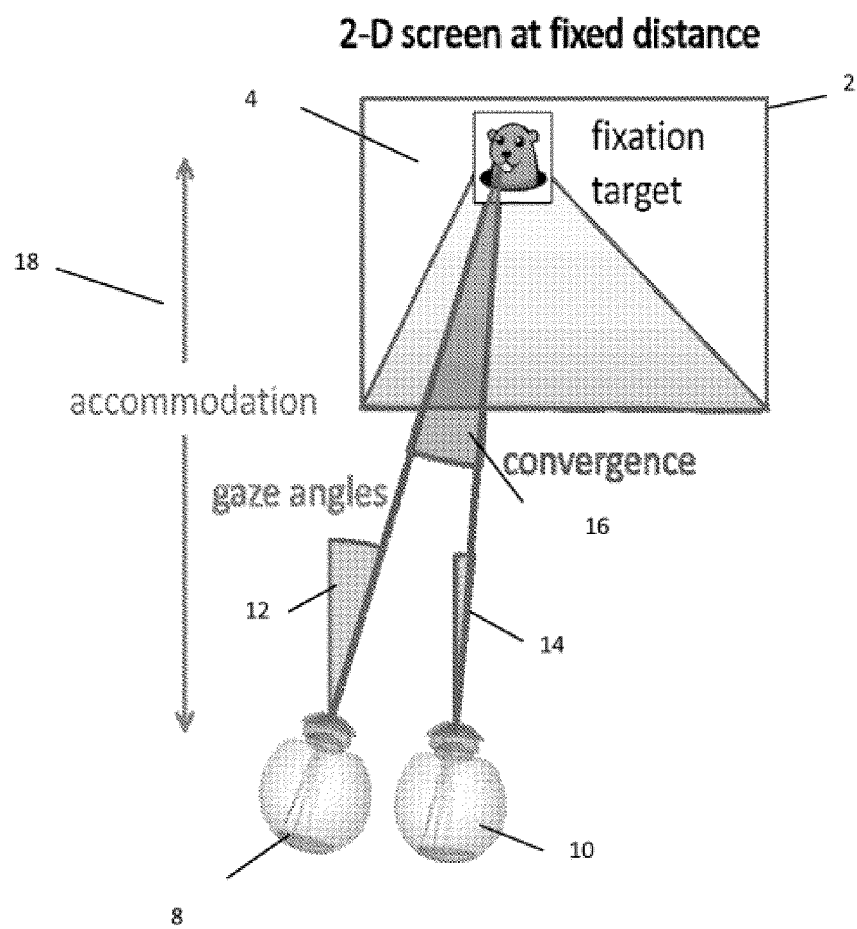
FIG. 2 is an example illustration of a prior-art screen-based visual field system.

Once the visual stimuli 326 and/or 328 are displayed to the subject 314, a response-capturing device 330 is used to track subject responses to the stimuli i.e., whether the subject observed the stimuli or not. In some embodiments, the response-capturing device 314 is a motion or gyro-sensor that tracks subject body movements (e.g., head movements or head nods) to determine whether a stimulus was seen or not. In other embodiments, the response-capturing device 314 is a traditional clicker or button (e.g., the button 107 in FIG. 1) that is clicked by the subject 314 to indicate whether he/she has seen a stimulus or not. In yet some other embodiments, the response-capturing device 314 is the eye sensor 302 that tracks eye movements for determining subject responses to the visual stimuli.

Figure 10:
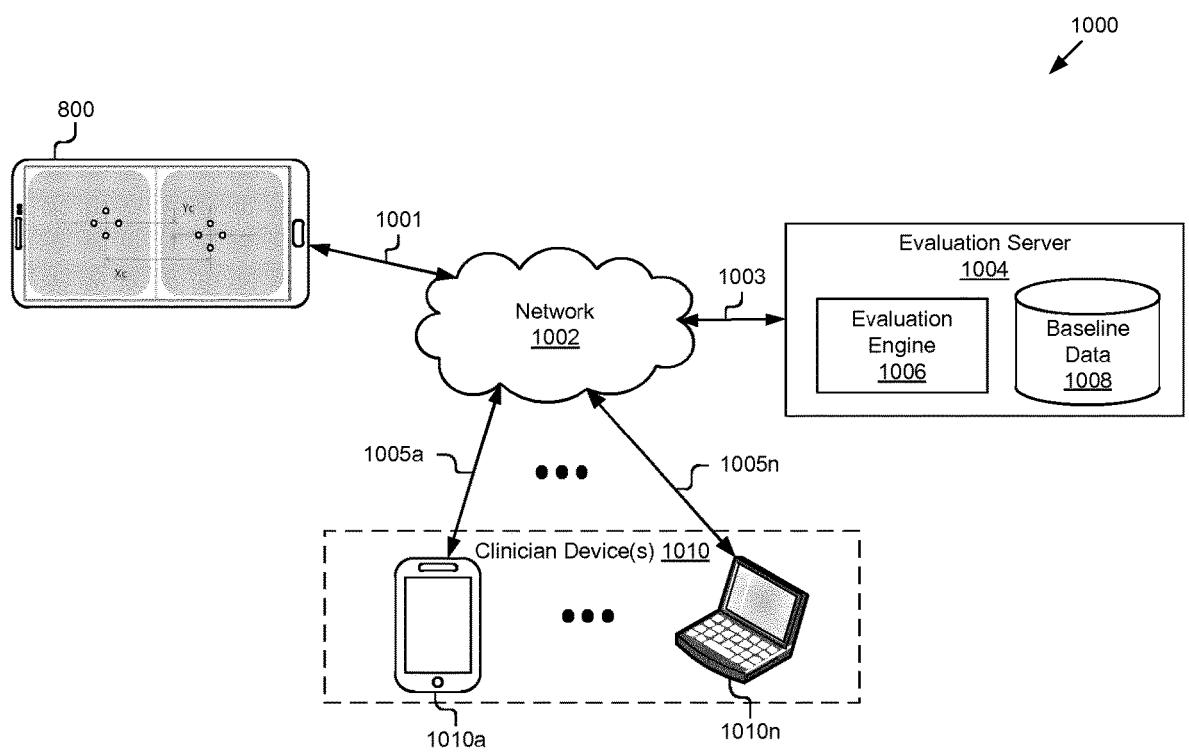
FIG. 10 is a block diagram of an example system for remotely testing a visual field condition of a subject.

Subject responses captured by the response-capturing device 330 are sent to the processor 316 for evaluating the subject's visual field and/or defect(s) associated with each eye of the subject 314. In some embodiments, the processor 316 may compare subject responses with baseline, normative, or reference data that include prior response data of the subject or response data of other subjects to assess a trend, change, and/or progression in the subject's visual field condition. In some embodiments, the processor 316 may demonstrate one or more defects associated with each eye of the subject using an image, as discussed in further detail below with respect to FIGS. 7A and 7B. The processor 316 may generate a display to present results of its evaluation (i.e., subject's visual field condition and/or defect(s) associated with each eye) to the subject 314 or a clinician or optionally send the results to one or more clinician devices (e.g., a clinician device 1010a as shown in FIG. 10) for display or further analysis. In some embodiments, the processor 316 may store results of its evaluation with date/time stamped in a data store (e.g., as baseline data 1008 (see FIG. 10)) for later access and/or retrieval purposes.

In some embodiments, the eye sensor 302, the processor 316, the display screen 320, and the response-capturing device 330 discussed above are parts of a single computing device which may be used for testing the visual field of a subject in a compact portable form factor. For instance, with reference to FIG. 8, a smartphone 800 includes: the eye sensor 302 for measuring the inter-eye distance and vertical positions of the subject eyes; the processor 316 for generating and displaying fixation targets and visual stimuli specific to each eye based on the inter-eye distance and eye positions; the display screen 320 for displaying the fixation targets and visual stimuli; and the response-capturing device 330 (e.g., a motion sensor) for capturing subject responses to the visual stimuli. In some embodiments, the smartphone 800 can be inserted into a virtual reality headset for performing a visual field test in a virtual reality setting, as discussed in further detail below with respect to FIG. 9.

Example Method

Figure 4:
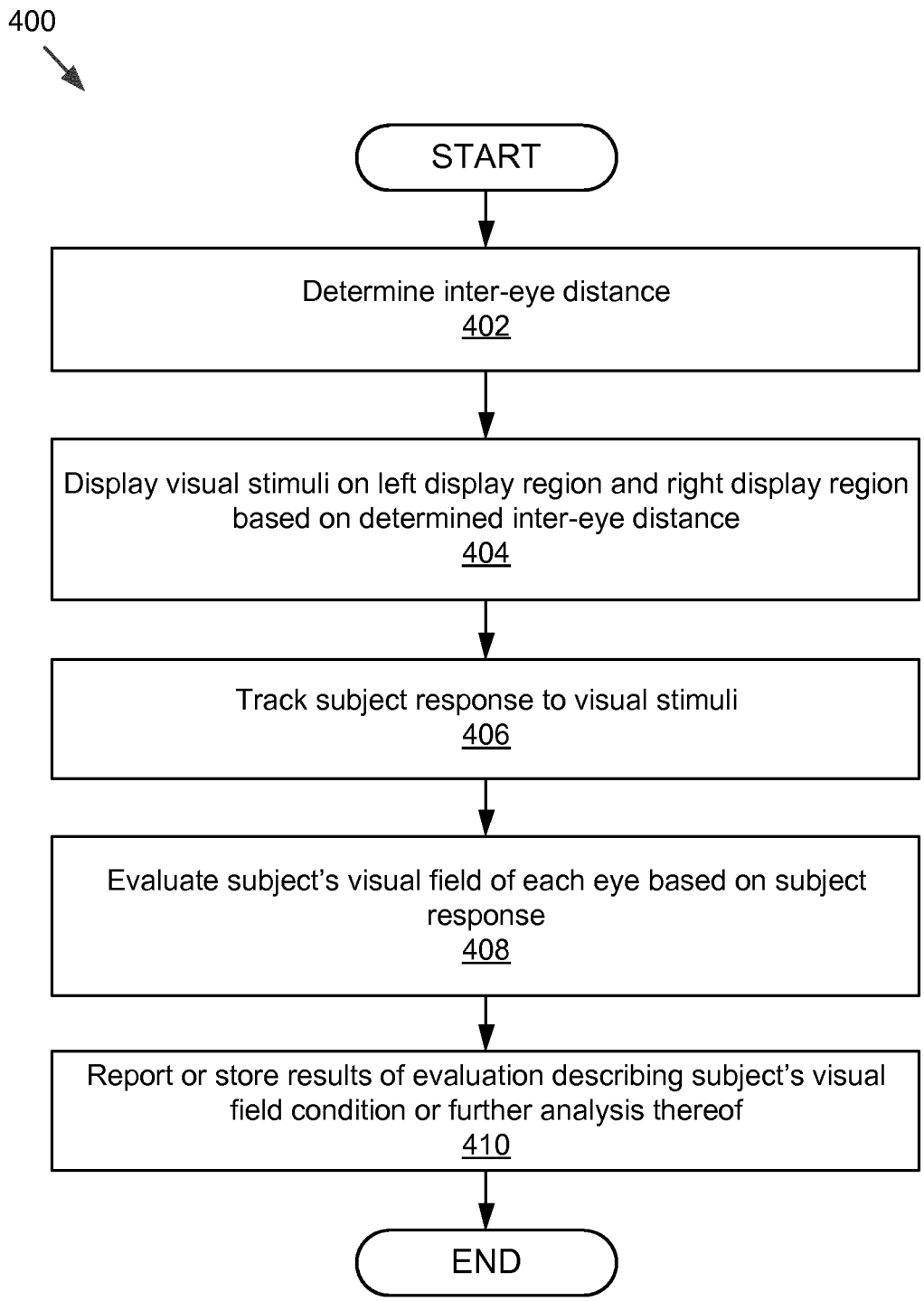
FIG. 4 is a flowchart of an example method for testing and evaluating a subject's visual field.

FIG. 4 is a flowchart of an example method 400 for testing and evaluating a subject's visual field according to one aspect of the present invention. The method 400 begins by first determining 402 an inter-eye distance of the subject under examination. This includes measuring the distance between the two eyes (i.e., horizontal inter-eye distance) and/or determining the vertical positions of the two eyes (i.e., vertical inter-eye distance), as shown and discussed for example in FIG. 3. Next based on the determined inter-eye distance, the method 400 displays 404 visual stimuli on a display screen (e.g., two-dimensional display screen), such as on the display screen 320 shown in FIG. 3. The display screen is split into two regions, namely a left display region that displays a fixation target and visual stimuli specific to the left eye of the subject and a right display region that displays a fixation target and visual stimuli specific to the right eye of the subject. In some implementations, the display screen may be embedded inside a virtual reality headset as discussed elsewhere herein. For instance, a smartphone comprising the display screen can be inserted into a virtual reality headset such that the display screen of the smartphone faces the wearer's eyes. In some embodiments, the virtual reality headset may be capable of producing a virtual reality effect of two separate display regions (i.e., the left and the right display regions) from the smartphone's display. In some embodiments, the method 400 can verify whether the subject's eye is looking at a fixation target without using a camera or gaze tracker, as discussed in further detail below with respect to the section entitled "Verification of subject attentiveness without a camera".

In block 406, the method 400 tracks the subject's responses to the displayed visual stimuli. Subject responses may include, for example, a head nod or movement, and/or any other body motion, which can be tracked using a motion sensor, such as the response-capturing device 330. It should be noted that other types of subject responses, such as pushing a response (e.g., mechanical clicker), verbal response, eye movements, etc., are also possible and are within the scope of the present invention.

Based on the subject responses to the visual stimuli, the method in block 408 evaluates the visual field of the subject and then in block 410, reports or stores results of the evaluation describing subject's field condition in a memory (e.g., the memory 1104) or a data store (e.g., the baseline data store 1008) for future access, retrieval, and/or analysis thereof. In some embodiments, the results of the evaluation can be displayed to the subject on the same display screen on which the subject was tested or the results can be sent to a clinician/administrator for display on his/her clinician device 1010 (see FIG. 10). The clinician/administrator may be a person who is skilled or an expert in the area of visual field testing.

It should be understood that the method described herein is not limited to the steps and/or operations discussed above and that other steps and/or operations are also possible and are within the scope of the present disclosure. It should also be understood that not every step described herein must be performed. Also, it should be noted that these steps or the present invention can be performed autonomously and/or independently without involving a clinician/administrator for administering a visual field test.

The following passages now discuss some additional features of the present invention:

Verification of Subject Attentiveness without a Camera

Verifying that an eye is looking at a predefined fixation target during testing traditionally requires a camera to supervise the eye during the examination. In one embodiment of the present invention, this verification is done without using an eye camera (e.g., eye sensor 302) or a gaze tracker. This may be achieved by first presenting visual stimuli to the subject in an early course of a visual field test and recording a baseline distribution of subject reaction times to those stimuli. Once the baseline distribution of the subject reaction times is established, test stimuli are presented to the blind spot a split second (e.g., a certain number of milliseconds, such as 200 ms) before the regular visual stimuli. If the subject now responds before his range of computed reaction times, it can be concluded that the subject response was given to the blind spot test stimuli instead of the regular visual stimuli and hence the subject was not looking at the predefined fixation target due to malfixation.

Eye-Blink Detection without a Camera

Eye blinks can be detected with a simple photosensor, which, in one embodiment, could be the eye sensor 302, pointing to at least one of the eyes. In some instances, the photosensor may be a separate component, which can be included in the system 300 for detecting eye blinks as discussed herein. Light refraction caused by a closed eyelid is different from the refraction caused when the eyelid is open. This difference can be detected by the photosensor as a means to detect eye-blinks. Detecting eye-blinks with such a photosensor is advantageous for low cost visual field testing systems.

Reducing Troxler and/or Blackout Effects

Figure 5:
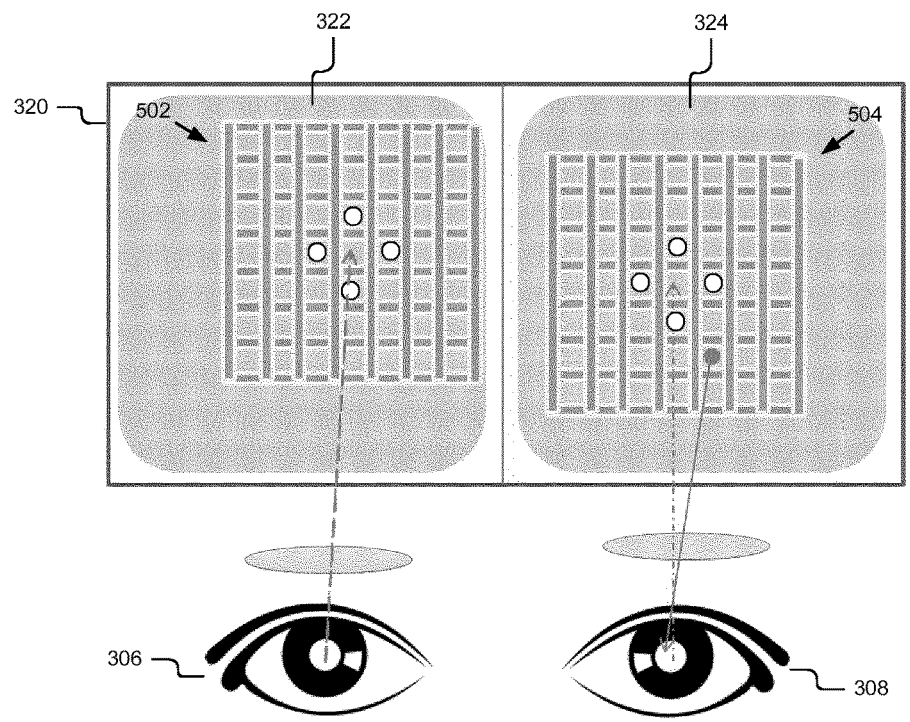
FIG. 5 illustrates enhancing background of a display with non-uniform content to avoid troxler and/or blackout effects to a subject.

In some embodiments, the background of each display region of the display screen 320 can be enriched with a pattern or any non-uniform content (see for example, non-uniform backgrounds 502 and 504 in the left display region 322 and the right display region 324, respectively in FIG. 5), which in combination with the natural micro-saccades prevents the eyes from producing irritating and confusing troxler and blackout effects. A troxler effect is one where an unchanging stimulus away from a fixation point will fade away and disappear when one fixates on the point even for a short period of time during the course of a visual field test. Micro-saccades are small eye movements that maintain continuous vision, or that ensure seeing a picture even if the eyes are looking at the same point over a longer period of time.

Elimination of Eye Patch

Figure 6:
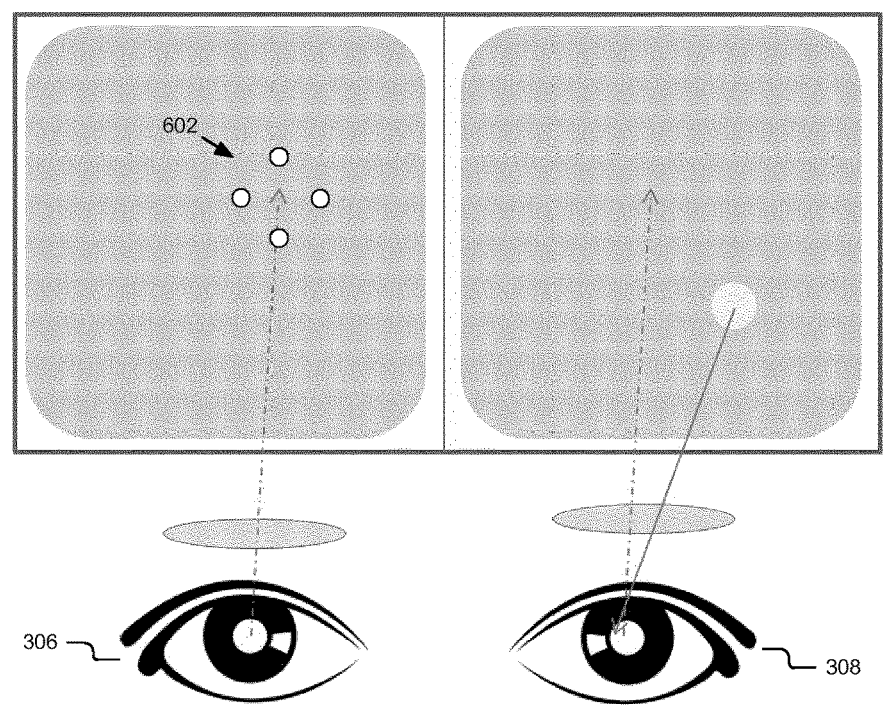
FIG. 6 is an example illustration where a non-examined eye is used for fixation purposes.

In one embodiment of the present invention, fixation targets and/or background images are shown to both eyes of a subject, but visual stimuli are displayed to only one eye. This results in improved fixation behavior for eyes with advanced and central visual field defects. This further prevents the eye from going through an independent light or dark adaptation cycle, as is the case when the non-examined eye is covered with an eye-patch in traditional visual field testing. By way of an example, FIG. 6 shows a scenario where visual stimuli 602 are shown to only the left eye 306, which is used for the fixation. In this example, the right eye 308, which is tested, has central visual field defects. No eye patch for the non-examined eye (i.e., eye to which visual stimuli are not shown) is used in such a scenario.

Image Based Visual Field Defect Demonstration

Figure 7A:
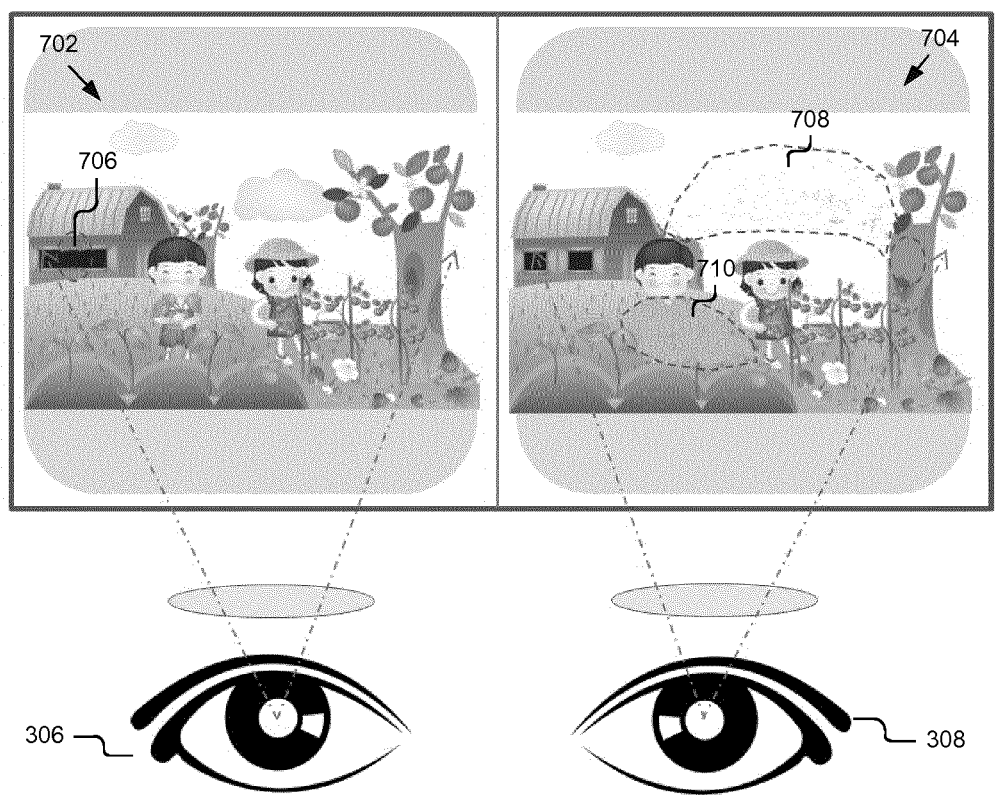
FIG. 7A is an exemplary way of showing visual field defects associated with each eye to a subject by making use of an image shown in FIG. 7B. In particular.
Figure 7B:

In some embodiments, the visual field condition of the subject 314 can be demonstrated using a photograph, an image, and/or a picture. Such an image may show various parts of the image that can be perceived or not perceived by each eye of the subject with his/her respective visual field. By way of an example, FIG. 7A shows an exemplary picture 702 showing parts perceived by the left eye 306 from the original picture 720 (see FIG. 7B) and an exemplary picture 704 showing parts perceived by the right eye 308 from the original picture 720. Specifically, the picture 702 shows that the left eye 306 incorrectly interprets the two windows in the barn (see FIG. 7B) as a single window, as shown by reference numeral 706. Thus, the left eye may have some side visual field defects. The picture 704 shows that the right eye does not recognize portions 708 and 710 of the original picture 720. Thus, the right eye may also have some central visual field defects. In some embodiments, the present invention can also demonstrate to a subject (e.g., the subject 314) using the same image 720 or a different image how his/her eye will interpret that image in the future (e.g., after 3 years) if defects in the eye are not treated. For instance, the image perceived and/or not perceived by each eye is based on an extrapolation of a known condition based on rate-of-change information. The rate-of-change information could either be based on prior data of the patient or based on population statistics for different conditions and treatments.

Increasing Dynamic Range of the Display

The human visual system typically has very high contrast sensitivity. Often a single intensity step of 1/256 in an 8 Bit greyscale system can be perceived, especially if the background intensity chosen is in the lower (darker) range of the display scale. True thresholding, however, requires detecting a threshold at which a contrast difference becomes visible/perceivable for the individual being tested. A traditional solution to this problem that has been used in standard perimetry for decades is to change the visual stimulus size (e.g. make the stimulus size smaller if the minimum intensity of a stimulus target can still be perceived on top of a given background intensity). This simply means reducing the number of pixels of the target that the individual needs to detect. In some embodiments, one or more of the following methods can be used to increase the dynamic range of a display, such as the display screen 320:

1. At low luminance levels, one color component can be added at a time to a stimulus instead of all the colors. Adding the color component does alter the luminance impression but not the color impression. By way of an example, if the background of the display has the RGB value {20, 20, 20}, the minimally brighter next "true" grey level would be {21, 21, 21}. However, taking into account the visibility for an individual observer, the dynamic range of the display can be increased by a factor of 3 by sequentially turning on the different colors, such as {20,20,20}->{20,20,21}->{20,21,21}->{21,21,21}.
2. In a stimulus that consists of multiple pixels, only a certain percentage or a subgroup of pixels can be switched to the next brighter light level to show the increased luminance and enhance the greyscales.
3. A further enhancement of the greyscales can be achieved by pulse width modulation i.e., by rapidly switching between two greyscale values.

The above methods can enhance the standard number of greyscales in low cost displays from 8 Bit (256 grey scales) to at least 10 bit and make them suitable for threshold testing.

Visual Field Testing in a Virtual Reality Environment

Figure 9:
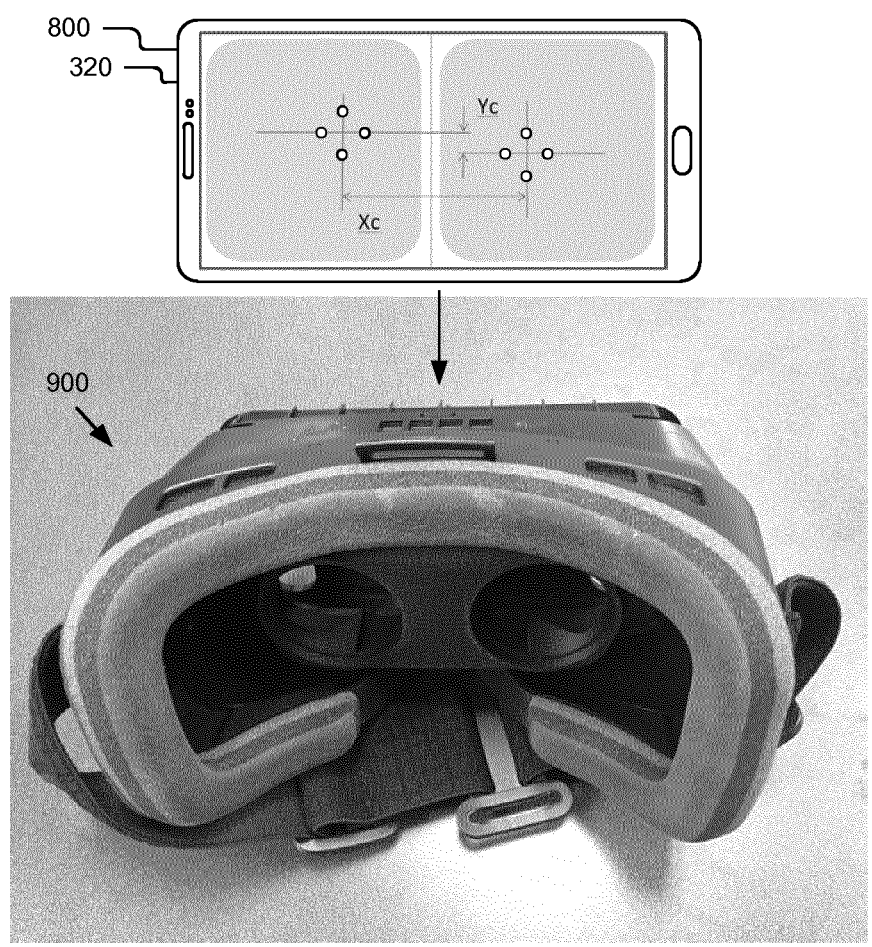
FIG. 9 illustrates use of the display device of FIG. 8 with a virtual reality headset for visual field testing in a virtual reality environment.

In some embodiments, the visual field test discussed herein can be performed in a virtual reality (VR) setting where a display, such as the display screen 320, is embedded inside a virtual reality headset, such as a headset 900 shown in FIG. 9. The headset 900 is a wearable headset that lets a wearer immerse in a VR environment. The headset 900 covers both eyes similar to a pair of ski goggles. In one embodiment of the present invention, the headset 900 uses the smartphone 800, which may be positioned or inserted into the headset 900 such that the display screen 320 of the smartphone 800 faces the wearer's eyes. In some embodiments, the virtual reality headset 900 may include optics that allow the screen 320 to appear at different distances from a wearer's eye and account for refractive error correction of the wearer. In some embodiments, the virtual reality headset 900 may be capable of providing an augmented reality experience to the wearer where one or more images/visual stimulus are superimposed on the wearer's view of the real world. By way of an example, the parts 706, 708, 710 in pictures 702 and 704 (see FIG. 7A) can be overlaid on top of the original picture 720 (see FIG. 7B) to demonstrate to the wearer the defect(s) associated with each eye.

To test a visual field of a headset wearer, the smartphone 800 within the virtual reality headset 900 generates a split-display (such as the split-display shown on the display screen 320 in FIG. 3). The split-display is generated based on first measuring an inter-eye distance and position of the wearer eyes as discussed elsewhere herein. The wearer may be instructed (via voice, sound, visuals, speech, etc.) to perform a task with respect to displayed fixation targets and stimuli. For example, the wearer is instructed to focus on a fixation target and respond when a visual stimulus is seen. Types of wearer responses with respect to a stimulus may include, for example, doing a head nod, and/or any other body motion, which is captured by the response-capturing device 330 (may be embodied in the smartphone 800 or the headset 900). Timing and accuracy of the wearer's responses or reactions to a given task are recorded and then evaluated by the smartphone's processor 316 to assess the wearer's visual field condition. In some embodiments, the evaluation of the wearer's visual field condition may be done remotely on a server, as discussed in further detail below with respect to FIG. 10.

Remote Evaluation of Visual Field Condition

FIG. 10 is a block diagram of an example system 1000 for remotely evaluating a visual field condition of a subject. As depicted, the system 1000 includes the smartphone 800, an evaluation server 1004, and one or more optional clinician devices 1010a through 1010n (individually or collectively referred to herein as 1010). These entities of system 1000 are communicatively coupled via a network 1002. The network 1002 may be a conventional type, wired or wireless, and may have numerous different configurations including a star configuration, token ring configuration, or other configurations. Furthermore, the network 1002 may include a local area network (LAN), a wide area network (WAN) (e.g., the Internet), Bluetooth™ communication networks, a cellular communications network, and/or other interconnected data paths across which multiple devices may communicate.

It should be understood that the present disclosure is not limited to this configuration and a variety of different system environments and configurations may be employed and are within the scope of the present disclosure. For instance, instead of the smartphone 800, any display device which is capable of generating a split-display (see FIG. 3) using the processor 316 and capable of capturing subject responses to the content displayed on the split-display can be used in the system 1000.

As depicted, the smartphone 800 is connected to the network 1002 via signal line 1001 for communicating with the evaluation server 1004 and/or one or more optional clinician devices 1010a through 1010n. For remote evaluation, the smartphone 800 acts as a gateway to relay subject response data (e.g., eye or body (e.g., head, neck, etc.) movements of a subject undergoing testing that are captured as the subject performs an action with respect to a visual stimulus displayed to the subject) via the network 1002 (e.g., WiFi, cellular data network, etc.) to the evaluation server 1004 for it to perform the evaluation. The evaluation server 1004 can be a hardware server that may include an evaluation engine 1006 for evaluating a condition of the subject's visual field based on the subject responses to the visual stimuli and then sending results of the evaluation via the network 1002 to the smartphone 800 or to the one or more clinician device 1010 for display. In some embodiments, the evaluation engine 1006 may perform its evaluation by comparing the subject response data with baseline data 1008 stored in the evaluation server 1004. As discussed elsewhere herein, the baseline data 1008 may include prior response data of a subject currently under testing whose prior data may be used to assess a trend, change, and/or progression in the subject's visual field condition. In some embodiments, the baseline data 1008 may also include response data of one or more other subjects for comparison purposes.

The clinician device(s) 1010 (any or all of 1010a through 1010n) are computing devices having data processing and data communication capabilities. The clinician devices 1010a through 1010n are communicatively coupled to the network 1002 via signal lines 1005a through 1005n respectively to receive results of the evaluation from the evaluation server 1004 or from the smartphone 800, and display them to their respective users. In some embodiments, a clinician device 1010 may be capable of evaluating a visual field condition of a subject by itself. For instance, a clinician device 1010 may receive subject response data from the subject's smartphone 800, process and/or evaluate the response data using a processor (e.g., processor 316) included in the clinician device 1010, and then present results of its evaluation on its display screen for display to its respective user (e.g., clinician, administrator, etc.). In some instances, the user using a clinician device 1010 may be a person who is skilled in the art of visual field testing.

In some embodiments, a clinician device 1010 is a smartphone (indicated by reference numeral 1010a), a laptop computer (as indicated by reference numeral 1010n), or any of a desktop computer, a netbook computer, a tablet, smartwatch, etc. It should be understood that the one or more clinician devices are shown with the dotted lines to indicate that these are optional and may not be part of the system 1000.

Example Computing Device

Figure 11:
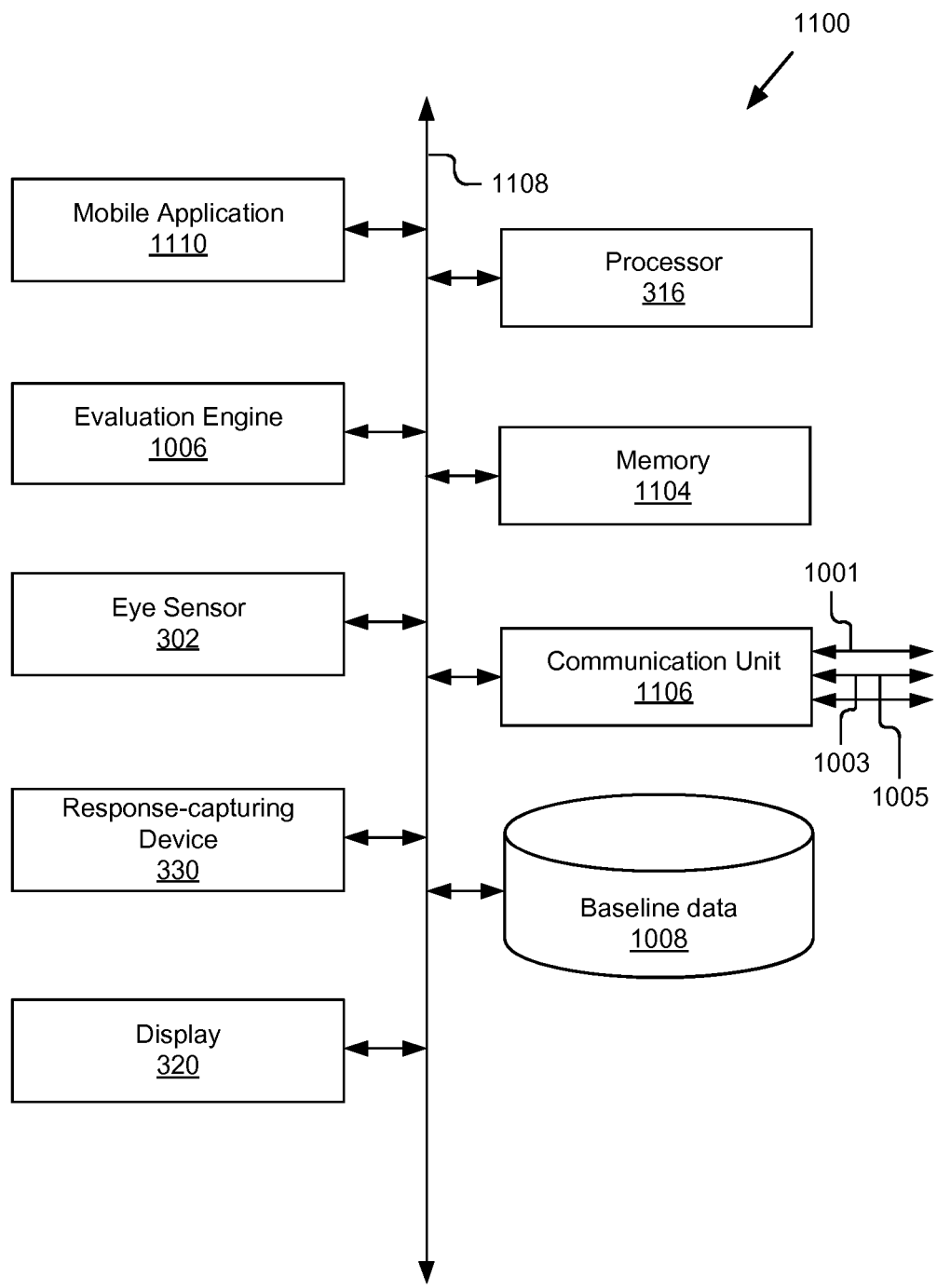
FIG. 11 is a block diagram of an example computing device, which may be representative of the display device shown in FIG. 8, the virtual reality headset shown in FIG. 9, a clinician's device, and/or a server.

FIG. 11 is a block diagram of an example computing device 1100, which may be representative of a computing device included in the smartphone 800, the headset 900, the evaluation server 1004, and/or the clinician device 1010. Depending upon the configuration, the computing device 1100 may include differing or some of the same components. For instance, in the case of smartphone 800, the computing device 1100 may include the processor 316, a memory 1104, a communication unit 1106, a mobile application 1110, the eye sensor 302, the response-capturing device 330, the display screen 320, and the baseline data 1008. In the case of the headset 900, the computing device 1100 may include the processor 316, the memory 1104, the eye sensor 302, and the response-capturing device 330. In the case of the evaluation server 1004, the computing device 1100 may include the processor 316, the memory 1104, the communication unit 1106, the evaluation engine 1006, and the baseline data 1008. In the case of the clinician device 1010, the computing device 1100 may include the components 316, 320, 1104, 1106, and 1110. It should be understood that the above configurations are provided by way of example and numerous further configurations are contemplated and possible.

As depicted, the various components of the computing device 1100 are communicatively coupled by a communication bus 1108. The bus 1108 can include a conventional communication bus for transferring data between components of a computing device or between computing devices. It should be noted that some of these components have already been discussed above and the description for these will not be repeated here.

The processor 316 may execute various hardware and/or software logic, such as software instructions, by performing various input/output, logical, and/or mathematical operations. The processor 316 may have various computing architectures to process data signals including, for example, a complex instruction set computer (CISC) architecture, a reduced instruction set computer (RISC) architecture, and/or architecture implementing a combination of instruction sets. The processor 316 may be physical and/or virtual, and may include a single core or plurality of processing units and/or cores. In some embodiments, the processor 316 may be capable of generating and providing electronic display signals to a display device, such as the smartphone 800, supporting the display of images, capturing and transmitting images, performing complex tasks including various types of feature extraction and sampling, etc. As discussed elsewhere herein, the processor 316 may be configured to evaluate a subject's visual field based on subject responses and further configured to report or store results of the evaluation describing the subject's field condition in a data store. In some embodiments, the processor 316 may be coupled to the memory 1104 via a data/communication bus to access data and instructions therefrom and store data therein. The bus 1108 may couple the processor 316 to the other components of the computing device 1100.

The memory 1104 may store instructions and/or data that may be executed by the processor 316. In some embodiments, the memory 1104 stores at least the mobile application 1110, the evaluation engine 1006, and the baseline data 1008. In some embodiments, the memory 1104 may also be capable of storing other instructions and data including, for example, an operating system, hardware drivers, other software applications, databases, etc. The memory 1104 is coupled to the bus 1108 for communication with the processor 316 and other components of the computing device 1100. The memory 1104 may include a non-transitory computer-usable (e.g., readable, writeable, etc.) medium, which can be any apparatus or device that can contain, store, communicate, propagate or transport instructions, data, computer programs, software, code, routines, etc. for processing by or in connection with the processor 316. A non-transitory computer-usable storage medium may include any and/or all computer-usable storage media. In some embodiments, the memory 1104 may include volatile memory, non-volatile memory, or both. For example, the memory 1104 may include a dynamic random access memory (DRAM) device, a static random access memory (SRAM) device, a flash memory, a hard disk drive, a floppy disk drive, a CD ROM device, a DVD ROM device, a DVD RAM device, a DVD RW device, a flash memory device, or any other mass storage device known for storing instructions on a more permanent basis.

In some embodiments, one or more of the smartphone 800, the evaluation server 1004, and the one or more clinician devices 1010 are located at the same or different locations. When at different locations, these components may be configured to communicate with one another through a wired and/or wireless network communication system, such as the communication unit 1106. The communication unit 1106 may include network interface devices (I/F) for wired and wireless connectivity. For example, the communication unit 1106 may include a CAT-type interface, USB interface, or SD interface, transceivers for sending and receiving signals using Wi-Fi™; Bluetooth®, or cellular communications for wireless communication, etc. The communication unit 1106 may be coupled to the network 1002 via the signals lines 1001, 1003, and 1005. The communication unit 1106 can link the processor 316 to a computer network, such as the network 1002 that may in turn be coupled to other processing systems.

The mobile application 1110 is storable in the memory 1104 and executable by the processor 316 of the smartphone 800 and/or a clinician device 1010 to provide for user interaction, receive user input, present information to the user, and send data to and receive data from the other entities of the system 1000 via the network 1002. In some embodiments, the mobile application 1110 may generate and present user interfaces (e.g., on the display screen 320) based at least in part on information received from the processor 316 and/or the evaluation server 1004. For example, a user/clinician may use the mobile application 1110 to receive results of an evaluation computed by the evaluation server 1004 on his/her clinician device 1010.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

Furthermore, the description can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof. Furthermore, it should be understood that the modules, routines, features, attributes, methodologies and other aspects of the present subject matter can be implemented using hardware, firmware, software, or any combination of the three.

The invention claimed is:

1. A method for testing a visual field condition of a subject, said method comprising:
   determining inter-eye distance of the subject, wherein the inter-eye distance includes horizontal and vertical eye distance;
   displaying visual stimuli on a left display region and a right display region of a two-dimensional display based on the determined inter-eye distance, said left display region configured to display content specific to the left eye and said right display region configured to display content specific to the right eye of the subject;
   tracking subject responses to the visual stimuli;
   evaluating the visual field of each eye of the subject based on the subject responses; and
   reporting or storing results of the evaluation describing the subject's visual field condition or a further analysis thereof.

2. The method as recited in claim 1, further comprising:
   displaying a predefined fixation target for each eye based on the determined inter-eye distance.

3. The method as recited in claim 2, wherein tracking the subject responses to the visual stimuli comprises verifying whether a subject's eye is looking at the fixation target, wherein said step of verification comprises:
   establishing a baseline distribution of subject reaction times to an initial set of visual stimuli presented to the subject;
   presenting test stimuli to blind spot of the subject a certain number of milliseconds before subsequent set of visual stimuli are displayed to the subject;
   determining subject reaction time in responding to the test stimuli or the subsequent set of visual stimuli; and
   comparing the subject reaction time with the baseline distribution of subject reaction times for verifying whether the subject's eye is looking at the fixation target.

4. The method as recited in claim 3 further comprising:
   regaining subject attentiveness by adjusting or moving the fixation target based on said verification.

5. The method as recited in claim 4, wherein the adjusted or moved fixation target reduces chances of troxler and/or blackout effects to the subject.

6. The method as recited in claim 3, wherein said step of verification is performed without using a camera, an eye-sensor, or a gaze tracking device.

7. The method as recited in claim 1, wherein the subject responses include head nods or head movements that are tracked by a motion sensor.

8. The method as recited in claim 1, wherein tracking subject responses comprise recording both the eyes of the subject.

9. The method as recited in claim 8 further comprising:
   iteratively measuring pupil diameter or area during the course of the visual field testing; and
   adjusting luminance level of the visual stimuli and/or display background based on the measurement to compensate for a change in pupil size.

10. The method as recited in claim 1, wherein one or more of the left display region and the right display region comprise a non-uniform background or content that in combination with natural micro-saccades substantially reduces troxler and/or blackout effects.

11. The method as recited in claim 1, wherein the subject's visual field condition is demonstrated using an image, said image showing parts of the image perceived and/or not perceived by each eye of the subject with said condition.

12. The method as recited in claim 1, wherein a visual stimulus is displayed to one eye while fixation targets are shown to both eyes to improve fixation behavior and to reduce chances of a non-examined eye to go through an independent light and dark adaptations cycles.

13. The method as recited in claim 1, wherein said method is performed autonomously and without involving a clinician or an administrator for administering the test.

14. The method as recited in claim 1, wherein instructions are given to the subject using one or more of sound, speech, and visual mediums to perform one or more tasks during the course of the visual field testing.

15. The method as recited in claim 1 further comprising:
   sending subject response data to a server, wherein said step of evaluating the subject's visual field is performed on the server.

16. A system for testing a visual field condition of a subject, said system comprising:
   an eye sensor for determining inter-eye distance of the subject, wherein the inter-eye distance includes horizontal and vertical eye distance;
   a display for displaying visual stimuli on a left display region and a right display region of the display based on determined inter-eye distance, said left display region configured to display content specific to left eye and said right display region configured to display content specific to right eye of the subject;
   a feedback means for tracking subject responses to the visual stimuli; and
   a processor for evaluating the subject's visual field of each eye based on the subject responses, said processor is further configured to report or store results of the evaluation describing the subject's visual field condition or a further analysis thereof.

17. The system as recited in claim 16, wherein the feedback means is a motion sensor that tracks head nods or movements as subject responses.

18. The system as recited in claim 16, wherein the display is a two-dimensional display of a smartphone.

19. The system as recited in claim 18 further comprising:
   a virtual reality headset for providing a virtual reality experience to the subject, wherein the virtual reality headset comprises the smartphone.

20. A system for testing a visual field condition of a subject, said system comprising:
   an eye sensor for determining inter-eye distance of the subject,
   a display for displaying visual stimuli on a left display region and a right display region of the display based on determined inter-eye distance, said left display region configured to display content specific to left eye and said right display region configured to display content specific to right eye of the subject;
   a feedback means for tracking subject responses to the visual stimuli; and
   a processor for evaluating the subject's visual field of each eye based on the subject responses, said processor is further configured to report or store results of the evaluation describing the subject's visual field condition or a further analysis thereof, wherein the inter-eye distance is determined by presenting to the subject, a moving left dot on the left display region and a moving right dot on the right display region and receiving the subject's response using the feedback means when the left and right dots appear on top of each other to the subject.

21. A system for testing a visual field condition of a subject, said system comprising:
- an eye sensor for determining inter-eye distance of the subject,
- a display for displaying visual stimuli on a left display region and a right display region of the display based on determined inter-eye distance, said left display region configured to display content specific to left eye and said right display region configured to display content specific to right eye of the subject;
- a feedback means for tracking subject responses to the visual stimuli; and
- a processor for evaluating the subject's visual field of each eye based on the subject responses, said processor is further configured to report or store results of the evaluation describing the subject's visual field condition or a further analysis thereof, wherein the inter-eye distance is determined by presenting to the subject a fine grid on each of the left and the right display regions and wherein the eye sensor records the subject's gaze direction as the subject focuses on the two grids and wherein the gaze direction is used to calculate the inter-eye distance.

* * * * *